(12) United States Patent
Rowe et al.

(10) Patent No.: US 9,007,175 B2
(45) Date of Patent: *Apr. 14, 2015

(54) BIOMETRIC IMAGING USING AN OPTICAL ADAPTIVE INTERFACE

(71) Applicant: Lumidigm, Inc., Albuquerque, NM (US)

(72) Inventors: Robert K. Rowe, Corrales, NM (US); Stephen P. Corcoran, Corrales, NM (US); Paul Bulter, Tijeras, NM (US)

(73) Assignee: Lumidigm, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,564

(22) Filed: Oct. 29, 2013

(65) Prior Publication Data
US 2014/0292484 A1  Oct. 2, 2014

Related U.S. Application Data

(63) Continuation of application No. 13/047,597, filed on Mar. 14, 2011, now Pat. No. 8,570,149.

(60) Provisional application No. 61/614,563, filed on Mar. 16, 2010.

(51) Int. Cl.
G06F 7/00 (2006.01)
G06K 9/00 (2006.01)
A61B 5/00 (2006.01)
A61B 5/117 (2006.01)
G07C 9/00 (2006.01)

(52) U.S. Cl.
CPC ............ *G06K 9/0004* (2013.01); *A61B 5/0075* (2013.01); *A61B 5/1172* (2013.01); *A61B 2562/146* (2013.01); *G07C 9/00158* (2013.01)

(58) Field of Classification Search
USPC ............ 340/5.82, 5.53; 382/315, 124; 396/15
See application file for complete search history.

(56) References Cited

U.S. PATENT DOCUMENTS 8,570,149 B2 * 10/2013 Rowe et al. .................. 340/5.82

* cited by examiner

*Primary Examiner* — Vernal Brown
(74) *Attorney, Agent, or Firm* — Marsh Fischmann & Breyfogle LLP; Kent A. Fischmann

(57) ABSTRACT

Embodiments of a biometric system with an optically adaptive interface are described. In some embodiments, an optically adaptive interface changes optical characteristics in response to the placement of a finger on the optically adaptive interface. In some embodiments, the optically adaptive interface can include an active layer and a surface layer. The active layer and the surface layer can have different optical properties. For example, one layer may be opaque and the other transparent, the two layers may have complementary colors, the two layers may have orthogonal polarization reflectors, one layer may be reflective and the other absorptive, etc. Moreover, the active layer can be a fluid with either high or low viscosity. For example, the viscosity can be such that the active layer fluid is either completely displaced or not displaced in locations corresponding to finger valleys.

21 Claims, 7 Drawing Sheets

BIOMETRIC IMAGING USING AN OPTICAL ADAPTIVE INTERFACE

CROSS-REFERENCE TO RELATED APPLICATIONS

This application is a continuation of U.S. application Ser. No. 13/047,597, entitled, "Biometric Imaging An Optical Adaptive Interface," filed Mar. 14, 2011, which claims the benefit of U.S. Patent Application No. 61/314,563, entitled, "Biometric Imaging Using An Optical Adaptive Interface," filed on Mar. 10, 2010. The contents of all of the above-noted applications are incorporated herein as if set forth in full and priority to all of these applications is claimed to the full extent allowable under U.S. law and regulations.

BACKGROUND OF THE INVENTION

"Biometrics" refers generally to the statistical analysis of characteristics of living bodies. One category of biometrics includes "biometric identification," which commonly operates under one of two modes to provide automatic identification of people or to verify purported identities of people. Biometric sensing technologies measure the physical features or behavioral characteristics of a person and compare those features to similar prerecorded measurements to determine whether there is a match. Physical features that are commonly used for biometric identification include faces, irises, hand geometry, vein structure, and fingerprint patterns, which is the most prevalent of all biometric-identification features. Current methods for analyzing collected fingerprints include optical, capacitive, radio-frequency, thermal, ultrasonic, and several other less common techniques.

Most existing fingerprint sensors rely on relatively high-quality contact between the finger and the sensor to obtain images. Obtaining adequate contact is both finicky and time-consuming because of factors related to individual characteristics of users of the sensors, the quality of the skin, and environmental variability. Ease of consistent fingerprint capture limits the effectiveness and scope of applications that utilize fingerprint biometrics for identity management.

SUMMARY

An optically adaptive interface is provided according to various embodiments of the inventions. An optically adaptive interface, for example, can be placed on the surface of a platen or any other device. An optically adaptive interface can change its optical characteristics in response to contact (or the presence) of a finger at the optically adaptive interface. This change can provide a different look and feel to the device depending on whether a user is interacting with the device or not. An optically adaptive interface can include thin layer(s) disposed on the surface of a biometric sensor platen. An optically adaptive interface can prevent a user from looking into the biometric sensor and seeing the illumination and/or imaging optics. An optically adaptive interface can also cut down on ambient light entering the sensor that can cause image degradation, sensor saturation, and/or other damage to the imaging sensor or loss of quality in the resulting image. An optically adaptive interface can also prevent light from within the sensor (e.g., from illumination optics) from exiting the sensor. Such light can be annoying or disruptive to a user. The optically adaptive interface can be used to improve the aesthetics of the sensor surface by allowing the sensor surface to have any color.

According to some embodiments, a biometric sensor can include a platen, an optically adaptive interface, an illumination subsystem, and an imaging subsystem. The optically adaptive interface can be disposed on the platen and can include a contact state and a non-contact state. In the non-contact state the optically adaptive interface is opaque and in the contact state a portion of the optically adaptive interface is substantially transparent. The illumination subsystem can be configured to illuminate a skin site of a purported individual when placed on the optically adaptive interface when the optically adaptive interface is in the contact state. The imaging subsystem can be configured to image the skin site when the optically adaptive interface is in the contact state.

In some embodiments, the default state of the optically adaptive interface is the non-contact state, and the optically adaptive interface changes from the non-contact state to the contact state in response to contact by the skin site. In some embodiments, the portion of the optically adaptive interface that is substantially transparent in the contact state occurs where the skin site is in contact with the optically adaptive interface. In some embodiments, the optically adaptive interface blocks light from the illumination subsystem from being transmitted through the optically adaptive interface. In some embodiments, the optically adaptive interface comprises a surface layer and an active layer. In some embodiments, the active layer comprises a fluid-like material and the surface layer is a thin film.

In some embodiments, a biometric sensor can include a housing, a platen defining a surface of the housing, an optically adaptive interface disposed on the platen, an illumination subsystem disposed within the housing, and an imaging subsystem disposed within the housing. The optically adaptive interface can include an opaque surface when viewed from an environment external from the housing. A portion of the optically adaptive interface changes optical properties when a skin site of an individual is placed on the optically adaptive interface allowing the illumination and imaging subsystems to produce a biometric image of the skin site.

In some embodiments, the optically adaptive interface blocks a user from viewing both the illumination subsystem and the imaging subsystem. In some embodiments, the optically adaptive interface changes optical properties at the location where the skin site is in contact with the optically adaptive interface. In some embodiments the change in the optical properties of the optically adaptive interface is a change from being opaque to substantially transparent. In some embodiments, the optically adaptive interface comprises a thin surface layer and an fluid-like active layer.

According to some embodiments, a biometric sensor can include a platen, an optically adaptive interface disposed on the platen, an illumination subsystem configured to illuminate portions of the platen and the optically adaptive interface, and an imaging subsystem configured to collect light from a skin site of a purported individual when placed on the optically adaptive interface. The optically adaptive interface can include two states: a non-contact state with a first optical condition, and a contact state with a second optical condition.

In some embodiments, in the contact state only a portion of the optically adaptive interface includes the second optical condition. In some embodiments, the illumination subsystem includes an optical element that filters light according to either the first optical condition or the second optical condition. In some embodiments, the optically adaptive interface comprises a surface layer and a fluid-like active layer. In some embodiments, the first optical condition the optically adaptive interface absorbs light from the illumination subsystem, and in the second optical condition at least a portion of the optically adaptive interface reflects light from the illumination subsystem.

In some embodiments, in the first optical condition the optically adaptive interface reflects light from the illumination subsystem, and in the second optical condition at least a portion of the optically adaptive interface absorbs light from the illumination subsystem.

In some embodiments, in the first optical condition the optically adaptive interface reflects light having a first wavelength, and in the second optical condition at least a portion of the optically adaptive interface reflects light having a second wavelength distinct from the first wavelength.

In some embodiments, in the first optical condition the optically adaptive interface absorbs light having a first wavelength, and in the second optical condition at least a portion of the optically adaptive interface absorbs light having a second wavelength distinct from the first wavelength.

In some embodiments, in the first optical condition the optically adaptive interface is substantially opaque, and in the second optical condition at least a portion of the optically adaptive interface is substantially transparent.

In some embodiments, the first optical condition the optically adaptive interface reflects light with a first polarization condition, and in the second optical condition at least a portion of the optically adaptive interface reflects light having a second polarization condition orthogonal with the first polarization condition.

DETAILED DESCRIPTION

Figure 1A:
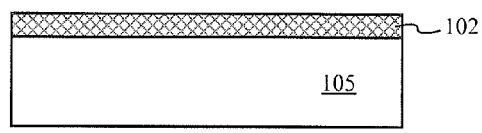
FIGS. 1A, 1B, 1C, and 1D show an optically adaptive interface in a non-contact state and a contact state according to some embodiments of the invention.
Figure 1B:
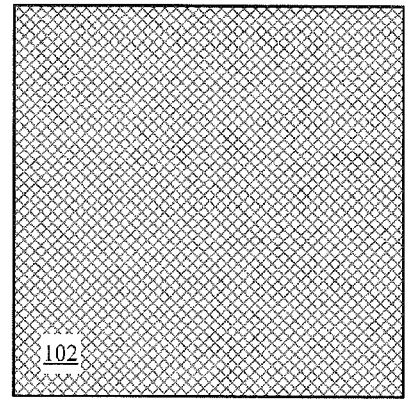

The ensuing description provides examples of embodiment(s) of the invention only, and is not intended to limit the scope, applicability or configuration of the disclosure. Rather, the ensuing description of the embodiment(s) will provide those skilled in the art with an enabling description for implementing these embodiments. Various changes may be made in the function and arrangement of elements without departing from the spirit and scope as set forth in the claims.

Introduction

An optically adaptive interface for biometric sensors is provided according to some embodiments of the invention. An optically adaptive interface, for example, can be placed on the surface of a platen, and can change its optical characteristics in response to contact (or the presence) of a finger at the optically adaptive interface. This change can provide a different look and feel to the device depending on whether a user is interacting with the device or not. An optically adaptive interface can include thin layer(s) disposed on the surface of a biometric sensor platen. An optically adaptive interface can prevent a user from looking into the biometric sensor and seeing the illumination and/or imaging optics. An optically adaptive interface can also cut down on ambient light entering the sensor that can cause image degradation, sensor saturation, and/or other damage to the imaging sensor or loss of quality in the resulting image. An optically adaptive interface can also prevent light from within the sensor (e.g., from illumination optics) from exiting the sensor. Such light can be annoying or disruptive to a user. The optically adaptive interface can be used to improve the aesthetics of the sensor surface by allowing the sensor surface to have any color.

The optically adaptive interface can be configured to have a contact state and a non-contact state that are optically distinct. These distinct optical responses can be complementary. For example, the two states can reflect light at different wavelengths, absorb light at different wavelengths, one state can absorb light while another reflects light, and the two states can reflect light with distinct (orthogonal) polarization, and can have opposite light transmission properties. In some embodiments, the imaging and/or illumination subsystems can include one or more optical elements that can be used to differentiate between light received from the optically adaptive interface under the two different states.

An optically adaptive interface can be used to increase the contrast between the ambient environment and the skin site when the skin site is present at the sensor. In some configurations, the optically adaptive interface can also be used to enhance fingerprint patterns. Various other improvements or useful configurations can also be used with the various embodiments disclosed herein.

For purposes of this disclosure, the terms "finger," "fingerprint," and "fingerprint image" are meant to include sites and images collected from a single finger, multiple fingers, intermediate finger joints, the palm, the entire palmar surface of the hand, and/or any other skin site on the body, as well as other animate or inanimate objects such as documents, barcodes, credentials, and the like.

The terms "multispectral imaging," "MSI," and "multi-imaging" refer to methods and systems for acquiring multiple images of a finger during a single measurement session, wherein at least two of the multiple images are collected under different optical conditions. Different optical conditions may include, but not limited to, different illumination wavelengths, different illumination angles (both in azimuth and elevation and may include elevations on either side of the optical critical angle defined by the sensor imaging surface and the air or other surrounding medium), different illumination polarization conditions, different imaging angles (both in azimuth and elevation and may include elevations on either side of the optical critical angle defined by the sensor imaging surface and the air or other surrounding medium), different imaging focal planes, different imaging spatial resolutions, different imaging temporal resolutions, different imaging polarization conditions, and other such conditions that substantially alter the resulting images. Also, unless otherwise specified, the angle of incidence, angle of illumination, angle of imaging, etc. can refer to the elevation and/or azimuth angle. Unless otherwise specified, the elevation angle is measured relative to the normal of the incident surface.

Figure 6A:
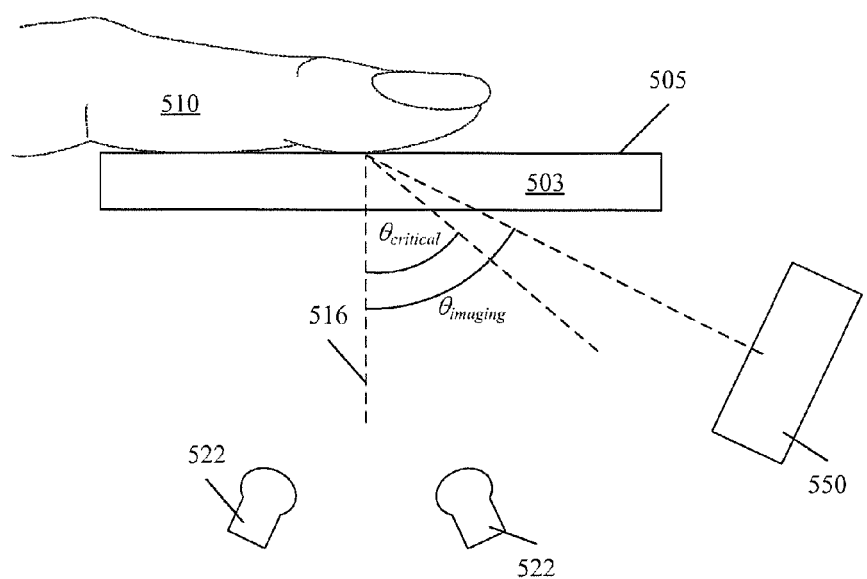
FIG. 6A is a TIR-imaging biometric sensor according to some embodiments of the invention.
Figure 6B:
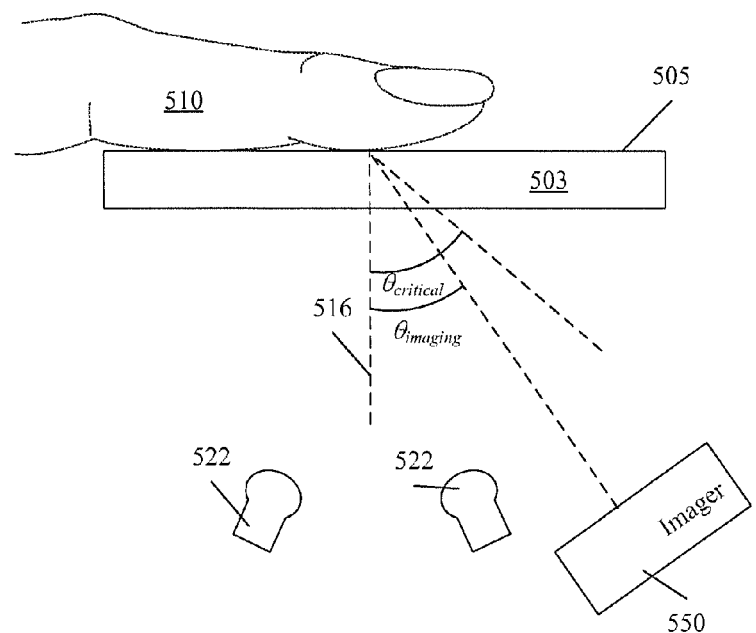
FIG. 6B is a direct-imaging biometric sensor according to some embodiments of the invention.

The terms "total internal reflectance imaging" and "TIR imaging" refer to a method of imaging wherein the optical axis of the imaging system lies at an angle relative to the normal of the sensor imaging surface and that is greater than the optical critical angle of that surface. A block diagram showing TIR imaging is shown in FIG. 6A. In this diagram, imager 550 images light from platen 505 at angle .theta.sub.imaging that is greater than the critical angle, .theta.sub.critical, as measured from normal 516 of facet 505. This is TIR imaging. Illumination sources 522 can be positioned at various elevation and azimuth angles and. FIG. 6B shows imager 550 that images light from platen 505 at angle .theta.sub.imaging that is less than the critical angle, .theta.sub.critical.

Figure 7A:
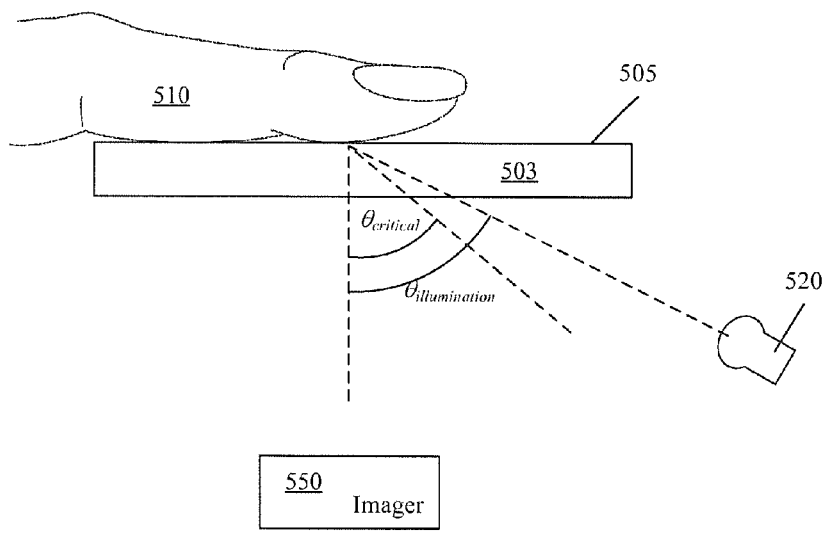
FIG. 7A is a TIR-illumination biometric sensor according to some embodiments of the invention.
Figure 7B:
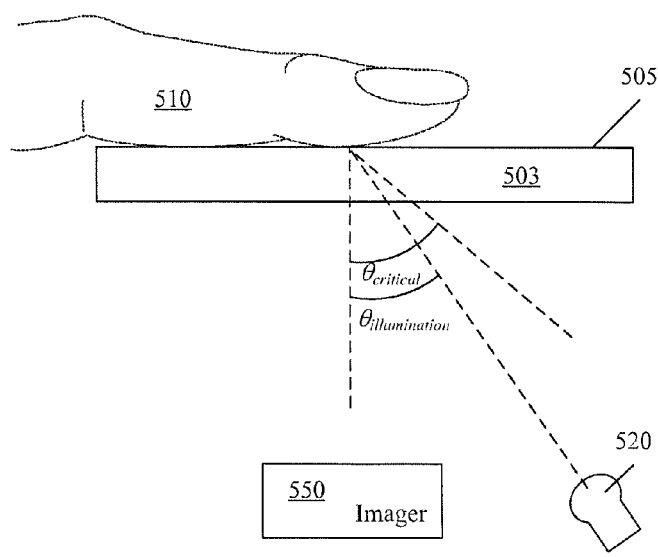
FIG. 7B is a direct-illumination biometric sensor according to some embodiments of the invention.

FIG. 7A illustrates TIR illumination. In this example, illumination source 520 illuminates platen 505 at an angle, .theta.sub.illumination, that is greater than the critical angle, .theta.sub.critical. FIG. 7B shows a non-TIR illumination system, with the illumination source 520 illuminating platen 505 at an angle, .theta.sub.illumination, that is less than the critical angle, .theta.sub.critical.

Various configurations of illumination and imaging are shown in FIGS. 6A, 6B, 7A and 7B. Embodiments of the invention can incorporate any combination of TIR imaging, direct imaging, TIR illumination, and direct illumination. Moreover, multiple illumination sources and/or imagers can be at multiple angles of elevation and/or aziumuth.

The critical angle is a function of the index of refraction of the two media on either side of an interface and is approximately 42 degrees for a glass-air interface. Because the optical axis of the TIR imaging system lies beyond the critical angle of the sensor surface, the surface acts as a mirror (as seen by the imager) when untouched, and can cease to act as a mirror in those locations in which a material with suitable optical characteristics comes into direct contact with the sensor surface.

In locations where a finger or other material contacts a sensor surface, a new critical angle is established. However, for purposes of the present disclosure, the term "critical angle" will refer to the angle established by the sensor (i.e., the platen surface) and the surrounding environment, which is assumed to be air for most purposes. Also, as known in the art, light will change angles at boundaries between media due to phenomena such as refraction, reflection, diffraction and other such effects. When a ray angle is referred to in the present application as being greater than or less than the critical angle, for example, the statement refers to the angle of the ray at the operative boundary such as the sensor imaging surface rather than the angle of the same ray at any other boundary or media, unless explicitly stated as such.

The term "direct imaging" refers to a method of imaging wherein the optical axis of the imaging system lies at an angle relative to the sensor imaging surface that is less than the optical critical angle of that surface. For example, the system shown in FIG. 7B is one sample of a direct imaging system.

The term "opaque" refers to the physical properly of absorbing, scattering or reflecting light incident on a material. A material can be opaque in the visual spectrum, in a specific spectrum, or within a wavelength band. A material is considered opaque if 90% of the light incident thereon is scattered, reflected or absorbed by the material. The term "transparent" refers to the physical property of allowing light to pass through a material. A material can be transparent in the visual spectrum or a specific wavelength band. A material is considered transparent if 90% of the light incident thereon is passed through the material. The term "translucent" refers to the physical property of allowing light of a specific wavelength or in a wavelength band to pass through a material.

Optically Adaptive Interface

An optically adaptive interface can be any layer(s), material(s), interface, condition, optical elements(s), coating(s), etc. configured to change optical properties in response to contact from a finger or the proximity of a finger near the optically adaptive interface. In some embodiments, an optically adaptive interface can have optical properties that change when a finger is placed on the optically adaptive interface. In some embodiments, the entire optically adaptive interface can change optical properties. In other embodiments, a portion (or portions) of the optically adaptive interface can change optical properties.

FIGS. 1A, 1B, 1C, and 1D show an example of optically adaptive interface 102. Optically adaptive interface 102 is opaque to light incident from within and without optically adaptive interface 102 in the non-contact state shown in FIG. 1B. This opacity can block light from traversing optically adaptive interface 102 and/or platen 105 from the interior of the device to the exterior and/vice-versa. That is, the opacity blocks light from traversing the optically adaptive interface. This opacity can keep users from viewing the internal structure of the device (e.g. imaging and/or illumination optics). This opacity can keep illumination light from beneath the platen from being seen by a user or keep such light from shinning in a user's eyes. This opacity can keep ambient light from flooding and damaging the imaging sensor. Optically adaptive interface 102 can have an aesthetically pleasing color, texture, appearance, etc. when viewed by a user.

Figure 1C:
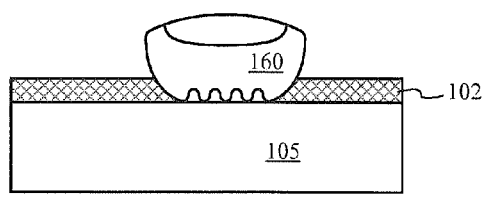
Figure 1D:
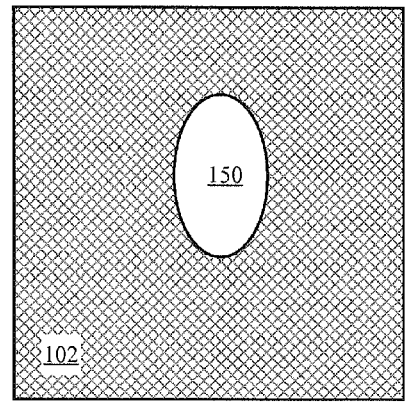

Optically adaptive interface 102 can then change from being opaque to transparent or partially transparent when finger 160 is placed in contact with optically adaptive interface 102 as shown in FIG. 1C. As shown in FIG. 1D, optically adaptive interface 102 can be transparent in contact region 150 where optically adaptive interface 102 is in contact with finger 160 or near where optically adaptive interface 102 is in contact with finger 160. This transparency can allow the illumination and imaging subsystems to then illuminate and image finger 160 through contact region 150. When finger 160 is in contact, TIR and/or direct illumination and/or imaging techniques can be used.

As another example, optically adaptive interface 102 can change from having an optical property in the non-contact state to having a complementary optical property when contacted by finger 160 in the contact state. Complementary optical properties can include a number of configurations. Complementary optical properties can produce distinct images when illuminated and imaged under the same conditions. The following chart shows examples of complementary optical properties for a contact state and a non-contact state of the optically adaptive interface. Various other complementary optical properties can be used. Wavelength #1 and wavelength #2 can include complementary colors such as, for example, red and green, orange and blue, purple and yellow, etc.

Figure 2:
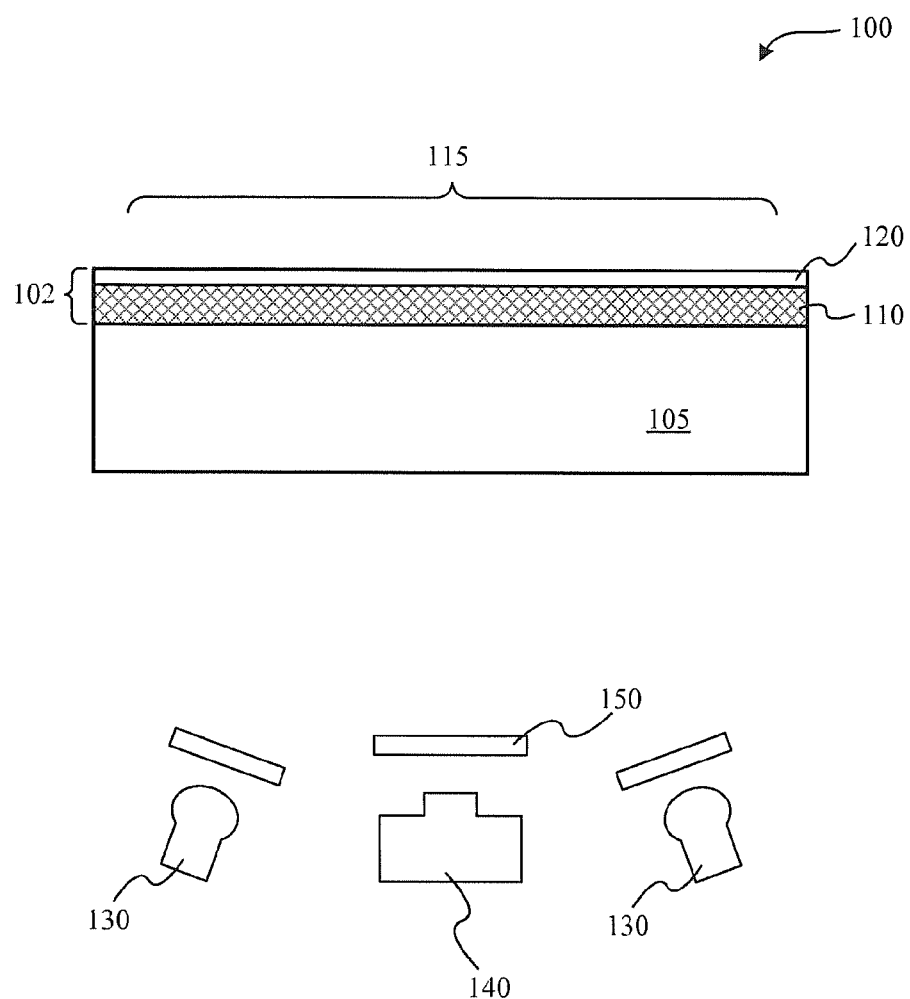
FIG. 2 shows an optically adaptive interface according to some embodiments of the invention.

TABLE-US-00001 Contact State Non-Contact state Reflective at wavelength #1 Reflective at wavelength #2 Reflective Absorptive Absorptive Reflective Absorptive at wavelength #1 Absorptive at wavelength #2 Opaque Transparent Reflects polarized light Reflects polarized light orthogonally from light reflected in contact state Reflects polarized light Filters polarized light orthogonally from light reflected in contact state Two Layer Optically Adaptive Interface FIG. 2 shows biometric sensor 100 with two layer optically adaptive interface 102 according to some embodiments of the invention. Optically adaptive interface 102 can include surface layer 120 that covers active layer 110. Optically adaptive interface 102 rests on platen 105. An individual can use biometric sensor 100 by placing a finger at imaging site 115 on the surface of optically adaptive interface 102. The sensor can include one or more illumination sources 130 and an imaging system 140. These illumination sources can be direct or TIR illumination sources. In some embodiments, one illumination source can illuminate the finger at an angle, $\theta_1$, while another illuminates the finger at an angle, $\theta_2$. Either or both of these illumination sources can be direct illumination sources such that $\theta_1 < \theta_{critical}$ and/or $\theta_2 < \theta_{critical}$. Where $\theta_{critical}$ is the optical critical angle. Or one of the two can be illumination sources that are used with total internal reflection proposes $\theta_1 < \theta_{critical}$ or $\theta_2 > \theta_{critical}$. Three or more illumination sources can be use in any combination of direct or TIR illumination configurations. The number, angle, and/or location of the illumination sources may be selected to achieve certain levels of illumination, to provide for multiple illumination wavelengths, to provide for multiple polarization conditions, to meet packaging requirements, and to meet other structural constraints of biometric sensor 100. Moreover, multiple illumination conditions can be used to provide multispectral imaging.

Illumination light passes from illumination source 130 toward imaging site 115. In some embodiments, the light can pass through illumination optics that shape the illumination to a desired form, such as in the form of flood light, light lines, light points, and the like. The illumination optics can include any combination of one or more lenses, polarizers, collimators, one or more filters, one or more mirrors, and/or other optical elements. In some embodiments, the illumination optics may also comprise a scanner mechanism to scan the illumination light in a specified one-dimensional or two-dimensional pattern. Illumination source 130 may comprise a point source, a line source, an area source, or may comprise a series of such sources in different embodiments. Illumination source 130 may be narrow band sources such as monochromatic LED's and laser diodes or may be broad band sources such as white-light LED's or incandescent sources. In the case where illumination source 130 comprises a series of sources, the series of sources may be of the same wavelength or different wavelengths. Illumination source 130 may be configured identically or they may differ from each other.

After the light passes through the optional illumination optics it passes through platen 105 toward optically adaptive interface 102. Optically adaptive interface can include active layer 110 and surface layer 120. These layers can have any number of properties and/or configurations. Multiple additional layers may also be used. Finger 160 can be imaged when placed at imaging site 115 on optically adaptive interface 102 layers. Light from illumination source 130 can then illuminate finger 160 so that reflected light and/or scattered light can be directed to imaging system 140. In some embodiments, this can be done through imaging optics 150. Platen 105 may be configured in such a manner that illumination light entering the platen will traverse platen 105 at the desired angles to illuminate imaging site 115.

Imaging system 140 can include any type of imager, such as a color imager, a camera, video camera, digital imager, RF imager, etc. Imaging optics 150 can include any combination of one or more lenses, polarizers, filters, mirrors, color filter arrays, and/or other optical elements. In conjunction with illumination source 130, imaging system 140 can collect images of a finger placed at imaging site 115. These images can be collected under a number of different illumination and/or imaging conditions and can produce one or more multispectral images.

Figure 5:
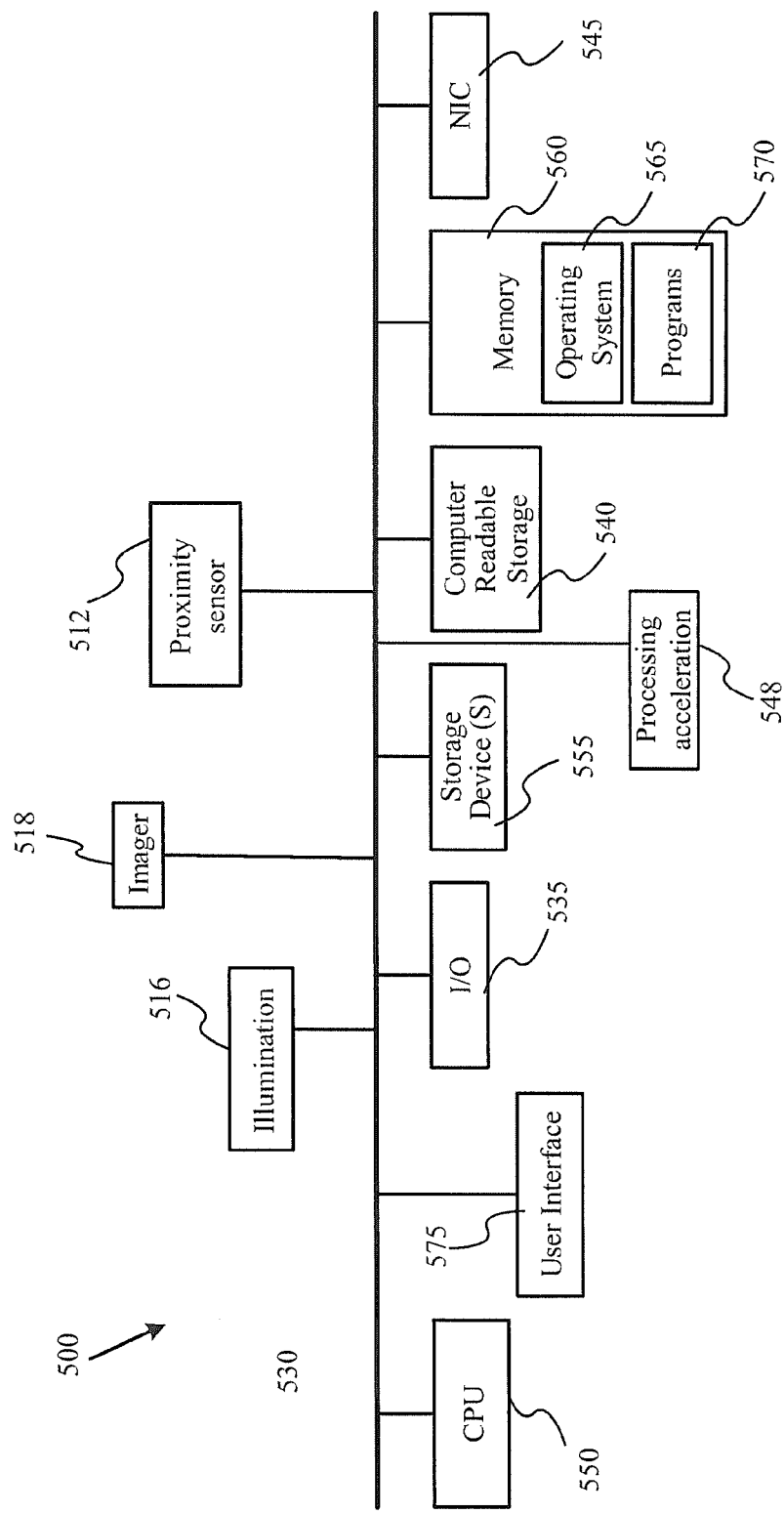
FIG. 5 is a block diagram of a biometric sensor computation unit according to some embodiments of the invention.

Biometric sensor 100 can include or be coupled with a biometric sensor computation system, like the one shown in FIG. 5. The biometric sensor computation system can be used to control imaging system 140 and/or illumination source 130. The biometric sensor computation system can include instructions, executable programs, routines, algorithms etc. that can be used to produce multispectral images, identify an individual, perform spoof detection, and/or check the liveliness of a finger from multispectral images. In particular, the biometric sensor computation system can derive spatially distributed multispectral characteristics from the one or more multispectral images.

In some embodiments, active layer 110 can include a fluid, fluid-like substance, paste, foam, dense liquid, gel, or gel-like substance. In some configurations, active layer 110 can a silicone, polyurethane, a copolymer, and/or a thermoplastic elastomer.

Surface layer 120 can include a thin elastic membrane, film or skin. Surface layer 120 can be a material made from an elastomer, acrylic, latex, artificial rubber, natural rubber, etc. In some embodiments, surface layer 120 can contain or hold a fluid or fluid-like active layer 110 and may be bound with platen 105. In some configurations, surface layer 120 can be painted on active layer 110. In some configurations, surface layer 120 can include a dissolved or diluted silicone, polyurethane, a copolymer, and/or a thermoplastic elastomer with a reflective pigment (e.g., metal paint such as silver, aluminum, bronze, titanium, titanium dioxide, etc.). This dissolved or diluted material can then be painted on active layer 110. Surface layer 120 can be made from a material that conforms with the ridges and valleys of a finger.

Opaque Active Layer and Transparent Surface Layer

Figure 3:
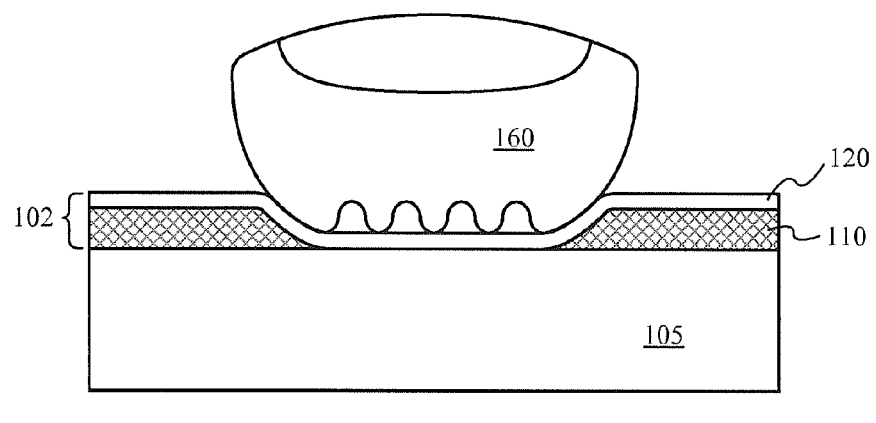
FIG. 3 shows an optically adaptive interface with a high viscosity active layer according to some embodiments of the invention.
Figure 3:
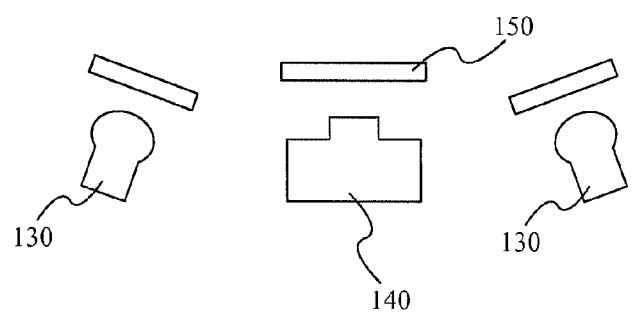

In one example, active layer 110 can include an opaque fluid (or fluid like material or gel) and surface layer 120 can include a transparent thin film as shown in FIG. 3. When finger 160 is pressed on surface layer 120, the portion of active layer 110 is pushed aside and surface layer 120 contacts platen 105. Active layer 110 disperses under pressure from finger 160 when finger 160 is presses surface layer 120 onto platen 105. In such embodiments, because surface layer 120 is transparent and active layer 110 is opaque, imaging system 140 can see finger 160 through surface layer 120 when finger 160 is pressed against platen 105. This occurs because opaque active layer 110 has been displaced. That is, optically adaptive interface 102 changes from being opaque to being transparent (or partially transparent) in the area where finger 160 is pressing against platen. With this change, a direct image and/or a TIR image of finger 160 can be captured. In some configurations, active layer 110 can have a relatively high viscosity (e.g., greater than 1.43 centipoise at 18 degrees centigrade).

Furthermore, when finger 160 is pressed against platen 105 finger 160 is visible surrounded by opaque active layer 110. The opaque portions of active layer 110 blocks light from the ambient environment while in the contact state.

Active layer 110 can include inks, dyes, colored polymers, etc. or a combination thereof to produce an opaque material. Various inks and/or dyes can be used to color active layer 110 and/or surface layer 120. In some embodiments, the inks or dyes can be added to ensure that material is sufficiently opaque and/or transmissive with the small thicknesses used in these layers.

In some embodiments, active layer 110 can have a color that is complementary with the color of skin to produce high contrast images between finger 160 and active layer 120. For example, active layer 110 can be a green or blue layer. In some embodiments, active layer 110 can have a color that is designed to complement the external environment. In such embodiments, a user can see surface layer 120 and active layer matches 110, or complements the external environment and/or the external components of biometric sensor 100 for aesthetic purposes.

Low Viscosity, Opaque Active Layer and Transparent Surface Layer

Figure 4:
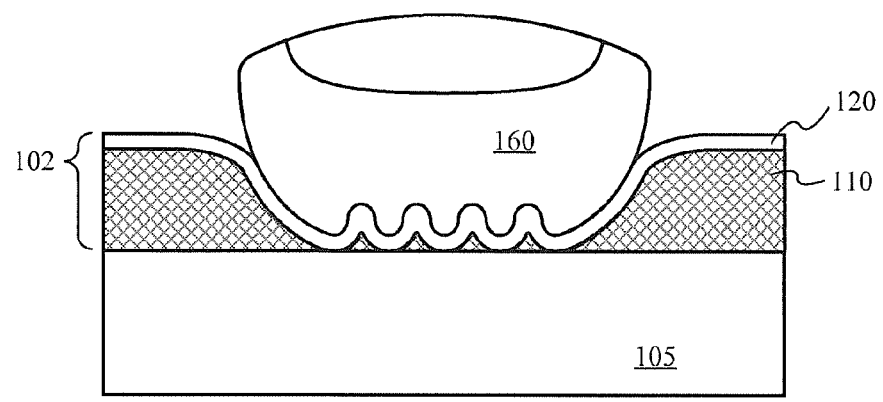
FIG. 4 shows an optically adaptive interface with a low viscosity active layer according to some embodiments of the invention.
Figure 4:
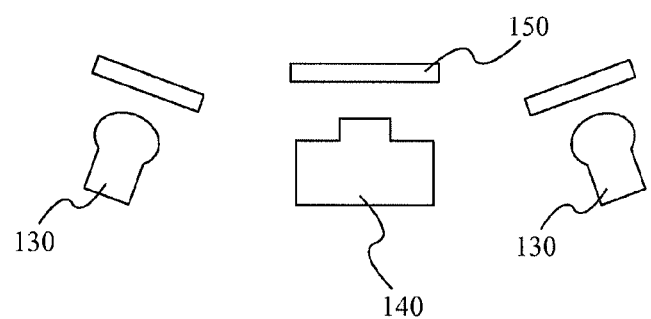

In another example, active layer 110 can include an opaque fluid or gel with a low viscosity and surface layer 120 can include a thin transparent film. The viscosity of the fluid can be low enough and/or the film thin and/or pliable enough that when finger 160 is pressed on surface layer 120, the fluid fills the valleys (or cracks) in finger 160 as shown in FIG. 4. That is, the stiffness of surface layer 120 and/or the fluid pressure of active layer 110 may be such that the active layer disperses only at points of contact (e.g., fingerprint ridges) but remain in the fine negative features (e.g., fingerprint valleys).

Imaging system 140 can then image ridges and valleys of finger 160 through surface layer 120. The valleys are not directly imaged. Instead, active layer 110 is imaged in the valleys of finger 160. Not only can active layer 110 be used to heighten the contrast between ridges and valleys, optically adaptive interface 102 can be useful for blocking the background environment from imaging in areas where finger 160 is not pressed against optically adaptive interface 102.

In some examples, active layer 110 can have a color that is complementary with the color of skin. For example, active layer 110 can be a green or blue layer. In some embodiments, active layer 110 can have a color that is designed to complement the external environment. In such embodiments, a user can see active layer 110 through transparent surface layer 120 and the color of active layer 110 matches, or complements the external environment and/or the external components of biometric sensor 100.

Active layer 110 can include inks, dyes, colored polymers, etc. or a combination thereof to produce an opaque material. Various inks and/or dyes can be used to color active layer 110 and/or surface layer 120. In some embodiments, the inks or dyes can be added to ensure that material is sufficiently opaque and/or transmissive with the small thicknesses used in these layers.

Low Viscosity, Opaque Active Layer and Opaque Surface Layer

In some embodiments, active layer 110 and surface layer 120 can both be opaque and can be made of materials having complementary on contrasting colors. Complementary colors are colors that when mixed produced a neutral color (e.g., grey, white or black). Moreover, complementary colors can provide a high contrast images of the two layers. For example, a low viscosity active layer 110 can be used with a color complementary to the color of surface layer 120. During imaging, the valleys can be identified by the color of active layer 110 and the ridges by the color of surface layer 120. Because the two layers have complementary colors, the contrast between the two will be heightened. As another example, active layer 110 can be a low viscosity layer and translucent at a single wavelength or wavelength band. The wavelength or wavelength band can be complementary to the color of surface layer 120. The valleys will then show up as a neutral color based on the combination of translucent active layer 110 and the color of surface layer 120. The ridges will show up only as the color of active layer 110.

In some configurations, imaging optics can include a color filter array. The colors of active layer 110 and surface layer 120 can be selected to coincide with a pixel color of the color filter array. In such configurations, finger valleys can be identified by isolating pixels corresponding with the color of active layer 110 and finger ridges can be identified by isolating pixels corresponding with the color of surface layer 120.

Surface Layer and Active Layer with Orthogonal Polarity Reflectors

In some embodiments, active layer 110 and surface layer 120 can include polarity reflectors with orthogonal polarizations. In some configurations, active layer can include a low viscosity fluid. In such configurations, ridges and valleys in a finger can be identified based on the polarization of the received light. For example, valleys can correspond with active layer 110 reflecting light of a given polarization and ridges can correspond with surface layer 120 reflecting light with an orthogonal polarization. In other embodiments, illumination source 130 illuminates skin site with unpolarized light. Imaging system 140 can include one or more polarizers (e.g., optical elements 150) that can filter the light reflected from finger 160 based on the polarization of active layer 110 and/or surface layer 120. In some embodiments, the polarization of the polarity reflector in the surface layer is orthogonal with a polarizer used to polarize light prior to imaging.

Surface Layer and Active Layer with Opposite Reflective and Absorption Characteristics In some embodiments, active layer 110 and surface layer 120 can have opposite reflective and absorption characteristics. Active layer 110 can have a low viscosity. For example, active layer 110 can be absorptive at a given wavelength (or wavelength band) and surface layer 120 can be reflective at the same wavelength (or wavelength band) or vice versa. In such embodiments, ridges and valleys in a skin site can be identified based on the reflective and/or absorption of light at the wavelength and/or wavelength band. For example, ridges will reflect light at the wavelength or in the wavelength band and valleys will absorb light at the wavelength or within the wavelength band. Illumination source 130 can illuminate finger 160 with light having the same wavelength or within the same wavelength band, for example, using a filter. Moreover, imaging system 140 can similarly image the wavelength or wavelength band, for example, using a filter or post process filter. A high contrast image will be produced with contrast between ridges and valleys.

Optically Adaptive Interface with Thermochromatic Material

In some embodiments, one or both of active layer 110 and surface layer 120 can include a thermochromatic material. A thermochromatic material is a material that changes optical properties in response to a change in temperature. A thermochromatic material can change optical properties in response to a change in temperature near the temperature of the human body. For example, the thermochromatic material can become opaque, transparent, change absorptive properties, or change reflective properties at specific wavelengths at temperatures between 93 and 130 degrees Fahrenheit. Thus, when finger 160 makes contact with a thermochromatic material, the material is heated by finger 160 to a higher temperature near the temperature of the human body. In response the material can become transparent, opaque, and/or change color.

In another configuration, an optically adaptive interface can include a single surface layer with thermochromatic properties disposed on a platen. In such configurations, the surface layer can normally be opaque, but can become transparent in response to contact with heat from finger 160. Direct and/or TIR imaging and/or illumination can be used to collect images of finger 160.

Optically Adaptive Interface with Conductive Materials

In some embodiments, either or both active layer 110 and surface layer 120 can include a conductive, semiconductive or resistive coating to act as mechanism for presence detection. The presence of a finger can be detected based on changes in capacitance, resistance, electric field effects or other means. Such a presence detection can provide a wake-up signal to other portions of the sensing system and/or other connected systems, for example, illumination system 130 and/or imaging system 140. For example, surface layer 120 and platen 105 may have conductive coating layers (e.g., transparent on at least the platen surface). When a finger touches the surface layer, some portions of surface layer 120 will directly contact the top of platen 105. This contact can complete an electrical circuit between the bottom of the surface layer 120 and the top of platen 105. This circuit can be monitored to provide a means to turn on the illumination, imaging, embedded processor, and/or other functions of biometric sensor system 100.

Biometric Sensor Computation System

FIG. 5 shows a block diagram of a biometric sensor computation system 500 including a computational device and peripheral devices according to one embodiment. The figure broadly illustrates how individual system elements may be implemented in a separated or more integrated manner. The biometric sensor computation system 500 is shown comprised of hardware elements that are electrically coupled via bus 530. Bus 530, depending on the configuration, may also be coupled with the one or more illumination systems 516 (e.g., illumination source 130), proximity sensor 512 (or presence sensor), and/or imager 518 (e.g., imaging system 140) according to various embodiments.

The hardware elements may include a central processing unit (CPU) 550, input/output device(s) 535, storage device 555, computer-readable storage 540, network interface card (NIC) 545, processing acceleration unit 548 such as a DSP or special-purpose processor, and memory 560. Computer-readable storage 540 may include a computer-readable storage medium and a computer readable medium reader, the combination comprehensively representing remote, local, fixed, and/or removable storage devices plus storage media for temporarily and/or more permanently containing computer-readable information. NIC 545 may comprise a wired, wireless, modem, and/or other type of interfacing connection and permits data to be exchanged with external devices.

Biometric sensor computation system 500 may also comprises software elements, shown as being currently located within memory 560, including an operating system 565 and other programs and/or code 570, such as a program or programs designed to implement methods described herein. Substantial variations in biometric sensor computation system 500 may be used in accordance with specific requirements. For example, customized hardware might also be used and/or particular elements might be implemented in hardware, software (including portable software, such as applets), or both. Further, connection to other computing devices such as network input/output devices may be employed.

What is claimed is:

1. A biometric sensor comprising: a platen; an optically adaptive interface disposed on the platen comprising a contact state and a non-contact state, wherein in the non-contact state the optically adaptive interface is opaque and in the contact state a portion of the optically adaptive interface is substantially transparent; an illumination subsystem configured to illuminate a skin site of a purported individual when placed on the optically adaptive interface when the optically adaptive interface is in the contact state; and an imaging subsystem configured to image the skin site when the optically adaptive interface is in the contact state.

2. The biometric sensor according to claim 1, wherein the default state of the optically adaptive interface is in the non-contact state, and the optically adaptive interface changes from the non-contact state to the contact state in response to contact by the skin site.

3. The biometric sensor according to claim 1, wherein the portion of the optically adaptive interface that is substantially transparent in the contact state occurs where the skin site is in contact with the optically adaptive interface.

4. The biometric sensor according to claim 1, wherein the optically adaptive interface blocks light from the illumination subsystem from being transmitted through the optically adaptive interface.

5. The biometric sensor according to claim 1, wherein the optically adaptive interface comprises a surface layer and an active layer.

6. The biometric sensor according to claim 5, wherein the active layer comprises a fluid-like material and the surface layer is a thin film.

7. A biometric sensor comprising: a housing; a platen defining a surface of the housing; an optically adaptive interface disposed on the platen; an illumination subsystem disposed within the housing; and an imaging subsystem disposed within the housing, wherein the optically adaptive interface comprises an opaque surface when viewed from an environment external from the housing, and a portion of the optically adaptive interface changes optical properties when a skin site of an individual is placed on the optically adaptive interface allowing the illumination and imaging subsystems to produce a biometric image of the skin site.

8. The biometric sensor according to claim 7, wherein the optically adaptive interface blocks a user from viewing both the illumination subsystem and the imaging subsystem.

9. The biometric sensor according to claim 7, wherein the optically adaptive interface changes optical properties at the location where the skin site is in contact with the optically adaptive interface.

10. The biometric sensor according to claim 7, wherein the change in the optical properties of the optically adaptive interface is a change from being opaque to substantially transparent.

11. The biometric sensor according to claim 7, wherein the optically adaptive interface comprises a thin surface layer and an fluid-like active layer.

12. A biometric sensor comprising: a platen; an optically adaptive interface disposed on the platen; an illumination subsystem configured to illuminate portions of the platen and the optically adaptive interface; and an imaging subsystem configured to collect light from a skin site of a purported individual when placed on the optically adaptive interface; wherein the optically adaptive interface comprises two states: a non-contact state with a first optical condition, and a contact state with a second optical condition.

13. The biometric sensor according to claim 12, wherein in the contact state only a portion of the optically adaptive interface includes the second optical condition.

14. The biometric sensor according to claim 12, wherein the illumination subsystem includes an optical element that filters light according to either the first optical condition or the second optical condition.

15. The biometric sensor according to claim 12, wherein the optically adaptive interface comprises a surface layer and a fluid-like active layer.

16. The biometric sensor according to claim 12, wherein in the first optical condition the optically adaptive interface absorbs light from the illumination subsystem, and in the second optical condition at least a portion of the optically adaptive interface reflects light from the illumination subsystem.

17. The biometric sensor according to claim 12, wherein in the first optical condition the optically adaptive interface reflects light from the illumination subsystem, and in the second optical condition at least a portion of the optically adaptive interface absorbs light from the illumination subsystem.

18. The biometric sensor according to claim 12, wherein in the first optical condition the optically adaptive interface reflects light having a first wavelength, and in the second optical condition at least a portion of the optically adaptive interface reflects light having a second wavelength distinct from the first wavelength.

19. The biometric sensor according to claim 12, wherein in the first optical condition the optically adaptive interface absorbs light having a first wavelength, and in the second optical condition at least a portion of the optically adaptive interface absorbs light having a second wavelength distinct from the first wavelength.

20. The biometric sensor according to claim 12, wherein in the first optical condition the optically adaptive interface is substantially opaque, and in the second optical condition at least a portion of the optically adaptive interface is substantially transparent.

21. The biometric sensor according to claim 12, wherein in the first optical condition the optically adaptive interface reflects light with a first polarization condition, and in the second optical condition at least a portion of the optically adaptive interface reflects light having a second polarization condition orthogonal with the first polarization condition.

* * * * *